(12) United States Patent
Bendelac et al.

(10) Patent No.: US 7,998,739 B2
(45) Date of Patent: Aug. 16, 2011

(54) METHODS OF ACTIVATING NKT CELLS

(75) Inventors: Albert Bendelac, Chicago, IL (US); Dapeng Zhou, Chicago, IL (US); Luc Teyton, Del Mar, CA (US); Paul Savage, Mapleton, UT (US)

(73) Assignees: The Scipps Research Institute, La Jolla, CA (US); Brigham Young University, Provo, UT (US); The University of Chicago, Chicago, IL (US)

( * ) Notice: Subject to any disclaimer, the term of this patent is extended or adjusted under 35 U.S.C. 154(b) by 801 days.

(21) Appl. No.: 11/218,906

(22) Filed: Sep. 2, 2005

(65) Prior Publication Data

US 2006/0073118 A1 Apr. 6, 2006

Related U.S. Application Data

(60) Provisional application No. 60/606,941, filed on Sep. 3, 2004.

(51) Int. Cl.
*C12N 5/07* (2010.01)
*A61K 31/70* (2006.01)
*C07K 14/00* (2006.01)

(52) U.S. Cl. .............................. 435/375; 514/25; 514/54

(58) Field of Classification Search ........................ None
See application file for complete search history.

(56) References Cited

U.S. PATENT DOCUMENTS

| 6,531,453 B1 | 3/2003 | Taniguchi et al. |
| 2003/0157135 A1 | 8/2003 | Tsuji et al. |
| 2004/0127429 A1 | 7/2004 | Tsuji |

FOREIGN PATENT DOCUMENTS

| EP | 0988860 | | 3/2000 |
| WO | 2006/029010 | * | 3/2006 |

OTHER PUBLICATIONS

Zhou (Curr. Protein and Peptide Science, 7: 325-333, 2006).*
Xia et al (Organic Letters, 8(24): 5493-5496, 2006).*
Bendelac et al (Annual Review of Immunology, 25: 297-336, 2007).*
Cantu et al. (Journal of Immunology, 2003, 170: 4673-4682).*
Cochran et al (Immunity 2000, 12: 2341-250).*
Vassan et al (Int. Immunol. 2007, 19(8): 943-951).*
Beaudoin, L. et al., Immunity (2002) 17:725-736.
Bendelac, A. et al., Nat. Rev. Immunol. (2001) 1:177-186.
Bendelac, A., Nat. Immunol. (2004) 5:557-558.
Benlagha, K. et al., J. Exp. Med. (2000) 191:1895-1903.
Brigl, M. et al., Annu. Rev. Immunol. (2004) 22:817-890.
Brigl, M. et al., Nat. Immunol. (2003) 4:1230-1237.
Cantu, C. et al., J. Immunol. (2003) 170:4673-4682.
Chiu, Y.H. et al., Nat. Immunol. (2002) 3:55-60.
Conzelmann, E. et al., Adv. Exp. Med. Biol. (1980) 125:295-306.
Dabrowski, J. et al., Biochemistry (1980) 19:5652-5658.
De Libero, G. et al., News Physiol. Sci. (2003) 18:71-76.
De Libero, Springer Semin. Immunopathol. (2000) 22:219-238.
Fischer, K. et al., Proc. Natl. Acad. Sci. USA (2004) 101:10685-10690.
Galili, U. et al., Subcell Biochem. (1999) 32:79-106.
Gumperz, J.E. et al., Immunity (2000) 12:211-221.
Hogquist, K.A. et al., Cell (1994) 76:17-27.
Honey, K. et al., Nat. Immunol. (2002) 3:1069-1074.
Kang, S.J. et al., Nat. Immunol. (2004) 5:175-181.
Kawano, T. et al., Science (1997) 278:1626-1629.
Keusch, J.J. et al., J. Biol. Chem. (2000) 275:25308-25314.
Kitamura, H. et al., "The natural killer T (NKT) cell ligand alpha-galactosylceramide demonstrates its immunopotentiating effect by inducing interleukin (IL)-12 production by dendritic cells and IL-12 receptor expression on NKT cells," J. Exp. Med. (1999) 189:1121-1127.
Ohshima, T. et al., Proc. Natl. Acad. Sci USA (1997) 94:2540-2544.
Park, S.-H. et al., J. Immunol. (1998) 160:3128-3134.
Park, S.H. et al., Nature (2000) 406:788-792.
Prigozy, T.I. et al., Science (2001) 291:664-667.
Sandhoff, K. et al., Phils. Trans. R. Soc. Lond. B. Biol. Sci. (2003) 358:847-861.
Sango, K. et al., Nat. Genet. (1996) 14:348-352.
Sheikh, K.A. et al., Proc. Natl. Acad. Sci. USA (1999) 96:7532-7537.
Smyth, M.J. et al., Nature Immunology (2001) 1:459:460.
Stanic, A.K. et al., Proc. Natl Acad. Sci USA (2003) 100:1849-1854.
Teneberg, S. et al., Glycobiology (2004) 14:187-196.
Van Der Vliet, H.J.J. et al., "Effects of α-galactosylceramide (KRN7000), interleukin-12 and interleukin-7 on phenotype and cytokine profile of human Vα24+Vβ11+T cells," Immunology (1999) 98:557-563.
Winau, F. et al., Nat. Immunol. (2004) 5:169-174.
Wu, D.Y. et al., J. Exp. Med. (2003) 198:173-181.
Yamashita, T. et al., Proc. Natl. Acad. Sci USA (2003) 100:3445-3449.
Zhou, D. et al., Science (2004) 303:523-527.
Zhou, X.T. et al., Org. Lett. (2002) 4:1267-1270.
Godfrey, D.I. et al., "The elusive NKT cell antigen—is the search over?" Science (2004) 306(5702):1687-1689.
Ogiso, M. et al., "Characterization of neutral glycosphingolipids in rat lens," Exp. Eye Res. (1995) 60:193-198.
Zhou, D. et al., "Lysosomal glycosphingolipid recognition by NKT cells," Science (2004) 306:1786-1789.
Smyth, M.J. et al., "NKT cells—conductors of tumor immunity?" Curr. Opin. Immunol. (2002) 14(2):165-171.
Van Dommelen, S.L.H. et al., "Activation of natural killer (NK) T cells during murine cytomegalovirus infection enhances the antiviral response mediated by NK cells," J. Virology (2003) 77(3):1877-1884.
Yu, K.O.A. et al., "Modulation of CD1d-restricted NKT cell responses by using N-acyl variants of alpha-galactosylceramides," Proc. Natl. Acad. Sci. (2005) 102(9):3383-3388.
Goodman & Gilman's The Pharmacological Basis of Therapeutics, Tenth Edition, Hardman and Limbird, editors, The McGraw-Hill Companies, Inc., New York (2001) 54-56.
Gupta, R.K. et al., "Adjuvants—a balance between toxicity and adjuvanticity," Vaccine (1993) 11(3):293-306.

* cited by examiner

*Primary Examiner* — Gerald Ewoldt
*Assistant Examiner* — Marianne DiBrino
(74) *Attorney, Agent, or Firm* — Merchant & Gould P.C.

(57) ABSTRACT

Provided are methods of activating an NKT cell which include a step of contacting the NKT cell with a sufficient amount of isoglobotrihexosylceramide (iGb3) to induce secretion of a cytokine from the NKT cell, stimulate proliferation of the NKT cell or upregulate expression of a cell surface marker on the NKT cell. Methods of activating an NKT cell population in a subject are also provided.

12 Claims, 7 Drawing Sheets

Scheme 1.

FIG. 7

SEQUENCE LISTING

```
<160> NUMBER OF SEQ ID NOS: 2

<210> SEQ ID NO 1
<211> LENGTH: 23
<212> TYPE: DNA
<213> ORGANISM: Mus sp.

<400> SEQUENCE: 1
attattatca ggctcataga agg                                              23

<210> SEQ ID NO 2
<211> LENGTH: 24
<212> TYPE: DNA
<213> ORGANISM: Mus sp.

<400> SEQUENCE: 2
ctagtttcgc accagcgtat attc                                             24
```

METHODS OF ACTIVATING NKT CELLS

CROSS-REFERENCE TO RELATED APPLICATIONS

The present application claims the benefit of priority from U.S. Provisional Application Ser. No. 60/606,941, filed Sep. 3, 2004, incorporated herein by reference.

STATEMENT REGARDING FEDERALLY SPONSORED RESEARCH

This invention was made with United States government support awarded by the National Institutes of Health, under grants PO1 AI053725, RO1 AI38339 and AI50847. The United States has certain rights in this invention.

INTRODUCTION

The CD1d molecule is a member of the CD1 family of $\beta 2$ microglobulin-associated molecules. In contrast to class I and II major histocompatibility complex (MHC) molecules that present peptide antigens to CD8+ and CD4+ T cells, respectively, CD1 molecules have evolved to capture and process both foreign and self lipid antigens for display to a particular subset of T cells known variously as NKT cells, CD1d-restricted T cells, invariant NKT or iNKT cells. NKT cells are characterized by self lipid reactivity and rapid effector responses. NKT cells express both natural killer (NK) cell surface markers and a conserved, semi-invariant T-cell receptor (TCR), specifically, V$\alpha$14-J$\alpha$18 paired with V$\beta$8 in mice, and V$\alpha$24-J$\alpha$18 paired with V$\beta$11 in humans.

NKT cells play an important role in a number of immune functions, including antimicrobial responses, antitumor immunity and regulating the balance between tolerance and autoimmunity. They express a natural memory phenotype typically associated with autoreactive recognition of conserved endogenous ligands.

A number of natural and synthetic agonists for NKT cells have been reported. The prototypical compound used to study NKT cell activation in vitro and in vivo is KRN7000, an $\alpha$-galactosylceramide ($\alpha$GalCer) originally isolated from marine sponge *Agelas mauritianus* (Kawano, et al., Proc. Natl. Acad. Sci. 278, 1626-29 (1997); see also U.S. Pat. No. 6,531,453 to Taniguchi et al.). Previous work has also established the requirement for lysosomal trafficking of CD1d molecules (Chiu, Y H et al., Nat. Immunol. 3, 55-60 (2002)), and the roles of lysosomal proteases (Honey, K et al., Nat. Immunol. 3, 1069-74 (2002)) and sphingolipid activator proteins, or saposins (Zhou, D et al., Science 303, 523-27 (2004); Kang S J et al., Nat. Immunol. 5, 175-81 (2004); Winau F et al., Nat. Immunol. 5, 169-74 (2004)). However, the natural ligand of the NKT cell receptor has not been previously identified.

SUMMARY OF THE INVENTION

Described herein is the inventors' discovery of the natural NKT cell receptor ligand, isoglobotrihexosylceramide (iGb3), a lysosomal glycosphingolipid of previously unknown function. Not only does this discovery provide an investigative tool to study and elucidate the function of NKT cells in multiple contexts (e.g., cancerous, infectious, and autoimmune disorders), but it also provides the basis for a novel therapeutic approach to these conditions as well.

Accordingly, in a first aspect, the invention provides methods of activating an NKT cell which include a step of contacting the NKT cell with a sufficient amount of iGb3 to induce secretion of a cytokine from the NKT cell, stimulate proliferation of the NKT cell or upregulate expression of a cell surface marker on the NKT cell.

In another aspect, the invention provides methods of activating an NKT cell in a subject which include a step of administering iGb3 to the subject in an amount sufficient to induce secretion of a cytokine from the NKT cell, stimulate proliferation of the NKT cell or upregulate expression of a cell surface receptor on the NKT cell.

BRIEF DESCRIPTION OF THE FIGURES

FIG. 6A depicts recombinant FLAG-tagged iGb3 enzyme detected by Western blot as indicated by arrow.

FIG. 6B depicts synthesized iGb3 as detected by HPTLC analysis. Lane 1, lactosylceramide; Lane 2, 48% of lactosylceramide was converted to iGb3 (indicated by arrow) after incubation with enzyme.

FIG. 6C provides NMR spectrum of enzymatically synthesized iGb3. Upper panel, downfield region of 500-MHz $^1$H-NMR spectrum (DMSO-d$_6$/2% D20, 35° C.) of Gal α1,3 Gal β1,4 Glc β1,1Cer product of in vitro enzymatic glycosylation of Gal β1,4 Glc β1,1Cer; lower panel, a spectrum of chemically synthesized iGb3 acquired under identical conditions. Arabic numerals refer to ring protons of residues designated by Roman numerals in the corresponding structures; Sph refers to protons of the sphingosine backbone; S, resonances corresponding to residual substrate; P, resonances corresponding to product. Impurity peaks are marked by asterisks.

DESCRIPTION OF SEVERAL EMBODIMENTS

Because of their role in regulating several widespread diseases, the nature and diversity of ligands recognized by NKT cells has been the subject of intense research and speculation. The present inventors have identified a single glycosphingolipid, isoglobotrihexosylceramide, referred to herein as "iGb3," as the primary endogenous ligand of both mouse Vα14 and human Vα24 NKT cells.

Accordingly, in one embodiment, the invention provides a method of activating an NKT cell by contacting the NKT cell with iGb3. The structure of iGb3 is represented by the following chemical formula:

"Activating an NKT cell" herein refers to inducing an observable effect in an NKT cell that is consistent with a cellular response to TCR binding by a stimulus. Observable effects of activation of NKT cells include secretion of cytokines, clonal proliferation of NKT cells and upregulation of expression of cell surface markers, for example, CD69 molecules, IL-12 receptors and/or CD40L molecules.

To activate an NKT cell in accordance with the present methods, the NKT cell is contacted with iGb3 in an amount sufficient to induce any of the above-listed observable effects. In vivo and ex vivo NKT cell activation are also contemplated, as discussed herein below.

A "cytokine," as the term is used herein and in the art, is an extracellular signaling protein or peptide that acts as a mediator in cell-to-cell communication. The term "cytokine" encompasses any such signaling molecule, and may include, but is not limited to, lymphokines, interleukins, tumor necrosis factors, granulocyte-macrophage colony activating factors and interferons.

Cytokines secreted by NKT cells may downregulate or moderate cell-mediated inflammatory reactions or exhibit other immunosuppressive or immunomodulatory properties. Examples of immunosuppressive or immunomodulatory cytokines may include, but are not limited to, IL-10, IL-4, and IL-12, IL-13 and GM-CSF. Alternatively, cytokines secreted by NKT cells may be involved in the amplification of inflammatory reactions. Inflammatory cytokines may include, but are not limited to IFN-γ, IL-2, IL-1, IL-6, IL-8, TNF, and TGF-β. It is appreciated that host responses to cytokines are largely multifactorial, and accordingly, particular cytokines listed above may evoke either a pro-inflammatory or an immunomodulatory response, depending on cellular context. Moreover, combinations of any of the above-noted cytokines may be secreted by NKT cells upon activation.

Methods for detecting and measuring levels of secreted cytokines are well-known in the art, and include, e.g., ELISA, Western blotting, FACS, etc.

NKT cell proliferation may also be induced upon activation by contact with iGb3. Proliferation is suitably measured in vitro by standard methods, e.g. $^3$H-thymidine or BrdU incorporation assays or trypan blue staining.

Upregulation of cell surface markers is also suitably observed upon activation of NKT cells. For example, CD69, CD25, CD40L and IL-12 receptors are upregulated upon activation of NKT cells. Immunologic methods, such as FACS, may be used to detect upregulation of cell surface markers, as well as other methods commonly employed in the art.

In the present methods, activation of NKT cells is typically initiated by contacting the TCR of the NKT cell with iGb3. iGb3 is may be presented by CD1d molecules on the surface of antigen presenting cells, such as dendritic cells, however, direct stimulation, i.e., contact of the TCR with "free" iGb3 is also contemplated. iGb3 may be provided in purified form or may be synthetic. As used herein, "purified" refers to compounds that have been separated from natural sources, although no particular degree of purity is required. As used herein, "synthetic" refers to compounds that have been produced according to a chemical synthetic process or produced by the action of an enzyme on a substrate. For example, iGb3 may be produced by the action of iGb3 synthase on lactosylcermamide, or may be produced by the action of β-hexosaminidases on iGb4, which is represented by the following chemical structure:

Alternatively, iGb3 is suitably synthetically prepared according to methods known in the art, or e.g., as described in Example 6 herein below.

iGb3 is generated as a transient intermediate during the synthesis of iGb4 in the Golgi apparatus and during the degradation of iGb4 in the lysosome (see FIG. 3A). The inventors have discovered that lysosomal iGb3 serves as the source of antigen for CD1d-restricted NKT cells. Accordingly, the present methods may comprise providing iGb4 as an "iGb3 precursor" to an antigen presenting cell, wherein it is degraded to iGb3 in the lysosome, associated with a CD1d molecule and shuttled to the plasma membrane for presentation to NKT cells.

Not to be bound by theory, it is hypothesized that lysosomal iGb3 might be dysregulated in type I diabetes and in cancer, where NKT cells exert protective functions mediated by Th2 and Th1 cytokines, respectively. Further, because endogenous rather than exogenous ligands induce protective IFN-γ release by NKT cells during infection by salmonella, iGb3 may activate NKT cells during infection, as well. Accordingly, the present invention contemplates activating an NKT cell population within a subject, or alternatively, activating an NKT cell population ex vivo and reintroducing the activated NKT cell population back into the subject. The subject is suitably a mammal, e.g., a human or a mouse.

Methods of activating an NKT cell population in a subject include administering iGb3 or an iGb3 precursor to the subject. Administration to a subject in accordance with some methods of the invention may include first formulating the iGb3 or iGb3 precursor with pharmaceutically acceptable carriers and/or excipients to provide desired dosages, etc. Suitable formulations for therapeutic compounds are known in the art. Administration may be carried out by any suitable method, including intraperitoneal, intravenous, intramuscular, subcutaneous, transcutaneous, oral, nasopharyngeal or transmucosal absorption, among others. Suitably, the compound is administered in an amount effective to activate an NKT cell population such that a therapeutic effect is achieved in the subject, e.g., an antineoplastic or antidiabetic effect.

Administration of iGb3 or an iGb3 precursor to a subject in accordance with the present invention appears to exhibit beneficial effects in a dose-dependent manner. Thus, within broad limits, administration of larger quantities of iGb3 or iGb3 precursor is expected to activate NKT cells to a greater degree than does administration of a smaller amount. Moreover, efficacy is also contemplated at dosages below the level at which toxicity is seen. Further, in practice, higher doses are generally used where the therapeutic treatment of a disease state is the desired end, while the lower doses are generally used for prophylactic purposes.

It will be appreciated that the specific dosage administered in any given case will be adjusted in accordance with the specific compounds being administered (e.g., iGb3 or an iGb3 precursor), the disease to be treated, the condition of the subject, and other relevant medical factors that may modify the activity of the drug or the response of the subject, as is well known by those skilled in the art. For example, the specific dose for a particular patient depends on age, body weight, general state of health, on diet, on the timing and mode of administration, on the rate of excretion, and on medicaments used in combination and the severity of the particular disorder to which the therapy is applied. Dosages for a given patient can be determined using conventional considerations, e.g., by customary comparison of the differential activities of iGb3 (or an iGb3 precursor) and of a known agent, such as by means of an appropriate conventional pharmacological protocol.

The maximal dosage for a subject is the highest dosage that does not cause undesirable or intolerable side effects. The number of variables in regard to an individual treatment regimen is large, and a considerable range of doses is expected. It is anticipated that dosages of iGb3 (or iGb3 precursor) in accordance with the present invention will reduce symptoms at least 50% compared to pre-treatment symptoms.

The following examples are provided to assist in a further understanding of the invention. The particular materials and conditions employed are intended to be further illustrative of the invention and are not limiting upon the reasonable scope of the appended claims.

EXAMPLES

Example 1

Experimental Methods

The following materials and methods were used in the experiments described in Examples 2-5.

Mice. β2M$^{-/-}$, from Jackson Labs (Bar Harbor, Mass.), CD1d$^{-/-}$ and CD1-TD "knock in" mice that carry the tail deleted CD1d molecule, αGa1A$^{-/-}$ mice were in the C57BL/6 background; Hexb$^{-/-}$, GM2$^{-/-}$ and GM3$^{-/-}$ mice were in the 129/Sv background. In all cases, littermates obtained from heterozygous matings were genotyped by PCR and used for comparative analysis. All mice were raised in a specific pathogen-free environment at University of Chicago according to the Institutional Animal Care and Use Committee guidelines.

Lymphocyte preparation and flow cytometry. Lymphocyte preparations, CD1d-αGalCer tetramers, and flow cytometry staining were done according to standard protocols, e.g., those described in Zhou D et al., Science 303, 523-27 (2004), incorporated herein by reference in its entirety.

CD1d-restricted T cell responses. Antigen presenting cells were mouse spleen cells cultured at $5 \times 10^5$ cells/well, mouse bone marrow-derived dendritic cells generated in the presence of GMC-SF and IL4, activated overnight with 10 ng/ml TNF-α and cultured at $5 \times 10^4$ cells/well, and human PBMC or GM-CSF/IL-4 cultured PBMC-derived dendritic cells cultured at $2.5 \times 10^5$ cells/well. NKT hybridomas were cultured at $5 \times 10^4$ cells/well and the human NKT line was cultured at $2.5 \times 10^5$ cells/well. Cytokines released in the culture supernatant were measured by standard ELISA for human IL-4 and IFN-γ (Pharmingen-Becton Dickinson, CA), and the indicator CTLL IL2 bioassay for mouse hybridomas. NKT hybridomas DN32.D3 (Vα14$^+$), TCBII (Vα14$^-$), TBA7 (Vα14$^-$) and the rat basophil leukemia RBL.CD1d transfectant line were used as described in Park, S-H et al., J. Immunol. 160 3128-34 (1998), incorporated herein by reference in its entirety. The human polyclonal Vα24Vβ11 NKT line was derived by repeated αGalCer stimulation of healthy human PBL in vitro and maintained by PHA and IL2 restimulation, and two different subclones, CD4 and DN, were used in experiments. *Griffonia Simplicifolia* isolectin B4 (IB4) was from Vector Laboratories, and anti-human CD1d mAb 51 was obtained from Dr. S. Porcelli. For stimulation with synthetic glycolipids, APCs were pulsed for 6 hours with various concentrations of lipids (from stock solution in DMSO), washed and incubated with NKT cell hybridoma or cell lines for 18-24 hours.

CD1d lipid loading and cell-free presentation assay. Purified complexes of CD1 d-GT were made and exchange of lipid in these complexes was quantified from isoelectric focusing gels as previously described by Cantu C III, et al., J. Immunol. 170, 4673-82 (2003), incorporated herein by reference in its entirety. Saposin-mediated loading of lipid was performed with recombinant human saposin B as described in Zhou D et al., Science 303, 523-27 (2004), incorporated herein by reference in its entirety, and with mouse saposin B. Recombinant mouse saposin B was expressed in a fly expression system and purified in the same manner used for production of mouse CD1d, described in Benlagha K, et al., J. Exp. Med 191, 1895-1903 (2000), incorporated herein by reference in its entirety. 2 μM mCD1d-GT was incubated with 25 μM of isogloboside in the presence or absence of 5 μM saposin B. Both mouse and human saposin B equally loaded iGb3 and iGb4 onto mCD1d-GT. Stimulation of the NKT cell hybridoma DN32.D3 was measured. Briefly, mouse CD1d protein was coated for 24 h at 1 μg/well in phosphate-buffered saline (PBS) on 96-well plates. Plates were washed three times with PBS and then incubated for another 24 h with a constant lipid concentration of 6 μg/ml and various concentrations of mouse saposin B. Plates were washed three times with PBS; then 2×10$^4$ hybridoma cells were added. Supernatants were collected after 24 h to measure IL-2 release.

Synthesis of iGb3. According to the mRNA sequence of a mouse homolog of iGb3 synthase enzyme (GenBank accession No: XM_144044), primers were designed to clone a soluble form of enzyme from cDNA prepared from mouse thymuses:

```
5' ATTATTATCAGGCTCATAGAAGG 3'     (SEQ ID NO: 1)

5' CTAGTTTCGCACCAGCGTATATTC 3'    (SEQ ID NO: 2)
```

A recombinant enzyme was produced using a Sf9 insect cell expression system, with an N-terminal FLAG peptide for immunopurification by anti-FLAG M2 agarose beads (Sigma). FLAG-tagged iGb3 was detected by Western blot, as shown in FIG. 6A.

To synthesize iGb3, purified recombinant iGb3 synthase was added to a 1 ml mixture of 2 mM UDP-galactose (Sigma), 0.2% Triton X-100, 200 μg lactosylceramide (Matreya) and 20 mM MnCl$_2$ in 100 mM Tris buffer (pH 7.4), overnight at 37° C. Glycolipids were purified by reverse phase C18 column chromatography and eluted by isocratial elution from 10% to 100% methanol. The reaction products were analyzed by HPTLC, as shown in FIG. 6B. Glycosphingolipid samples were deuterium exchanged by repeated addition of CDCl3-CD3OD 1:1, sonication, and evaporation under dry nitrogen, and then dissolved in 0.5 mL DMSO-d$_6$/2% D$_2$O, that contained 0.03% tetramethylsilane as chemical shift reference. 1-D 1H-NMR spectra, shown in FIG. 6C, were acquired at 35° C. on a Varian Inova 500 MHz spectrometer, with suppression of residual HOD by presaturation pulse during the relaxation delay. The spectral data for the biosynthetic product were interpreted by comparison to those of relevant glycosphingolipid standards acquired under virtually identical conditions, as well as to previously published data.

Figure 6:
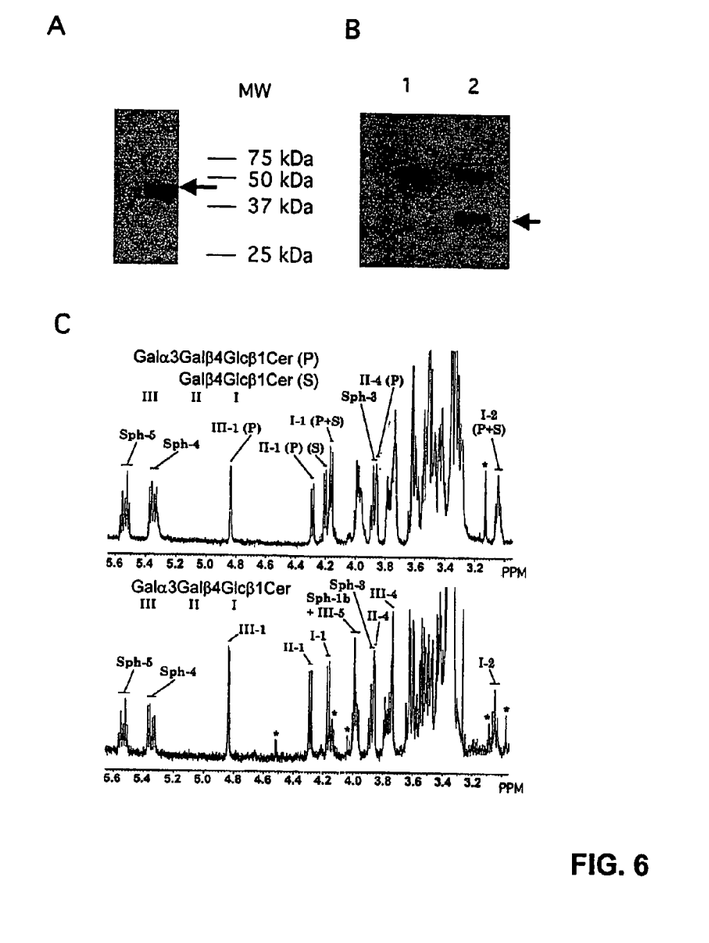

1-D $^1$H-NMR spectrum of the enzyme incorporated iGb3. As shown in FIG. 6C, 1-D $^1$H-NMR spectrum of the purified reaction mixture clearly exhibited H-1 resonances, consistent with the presence of a CTH product containing a non-reducing terminal α-galactose residue, at levels approximately 40-50% of those of the CDH acceptor substrate. Comparison with $^1$H-NMR data published for various natural CTH variants, and for synthetic standards of the isomeric CTH variants Gal α1,4 Gal β1,4 Glc β 1,1 Cer (Gb3) and Gal α1,3 Gal β1,4 Glc β1,1 Cer (iGb3), indicated that the product is iGb3. As shown FIG. 6, diagnostic resonances for H-1 of Galα3, Galβ4, and Glcβ1 of iGb3 are observed at 4.836 ppm ($^3J_{1,2}$=3.7 Hz), 4.288 ppm ($^3J_{1,2}$=7.8 Hz), and 4.168 ppm ($^3J_{1,2}$=7.8 Hz), respectively. In contrast, H-1 of Galα4, Galβ4, and Glcβ1 of Gb3 were observed at 4.789 ppm ($^3J_{1,2}$=3.7 Hz), 4.257 ppm ($^3J_{1,2}$=7.6 Hz), and 4.163 ppm ($^3J_{1,2}$=7.6 Hz), respectively (data not shown). The former set of H-1 resonances were clearly recapitulated in the spectrum of the partially converted product; thus, in addition to H-1 resonances at 4.205 ppm ($^3J_{1,2}$=7.0 Hz) and 4.163 ppm ($^3J_{1,2}$=7.7 Hz), corresponding to H-1 of Galβ4 and Glcβ1 of the CDH substrate, H-1 resonances were observed at 4.836 ppm ($^3J_{1,2}$=3.7 Hz) and 4.288 ppm ($^3J_{1,2}$=7.3 Hz), identical to those of Galα3 and Galβ4 of iGb3 (the chemical shift of Glcβ1 H-1 is not significantly affected by the addition of the terminal Galα3 residue, appearing at 4.166 ppm, ($^3J_{1,2}$=8 Hz). Additional diagnostic resonances for the iGb3 structure can be observed for H-5 of Galα3, H-4 of Galβ4, and H-4 of Galα3 at 3.992, 3.857, and 3.739 ppm, respectively, in both spectra. The comparable resonances for H-5 of Galα4, H-4 of Galβ4, and H-4 of Galα4 in the Gb3 structure were observed at 4.074, 3.791, and 3.744 ppm, respectively (data not shown). These chemical shift differences can all be rationalized on the basis of the mutual shielding/deshielding influences of atoms of the two Gal residues joined to each other by α 1,3 versus α1,4 linkages in iGb3 and Gb3, respectively. The characteristic pseudotriplet for H-5 of Galα4 in Gb3 is conspicuously absent from the spectra of both biosynthetic and synthetic iGb3 in the vicinity of 4.074 ppm, and is instead overlapped with the Sph-1b resonance observed at ~3.98 ppm. Thus, the identity of the biosynthetic product is clearly demonstrated as iGb3.

Example 2

Figure 1:
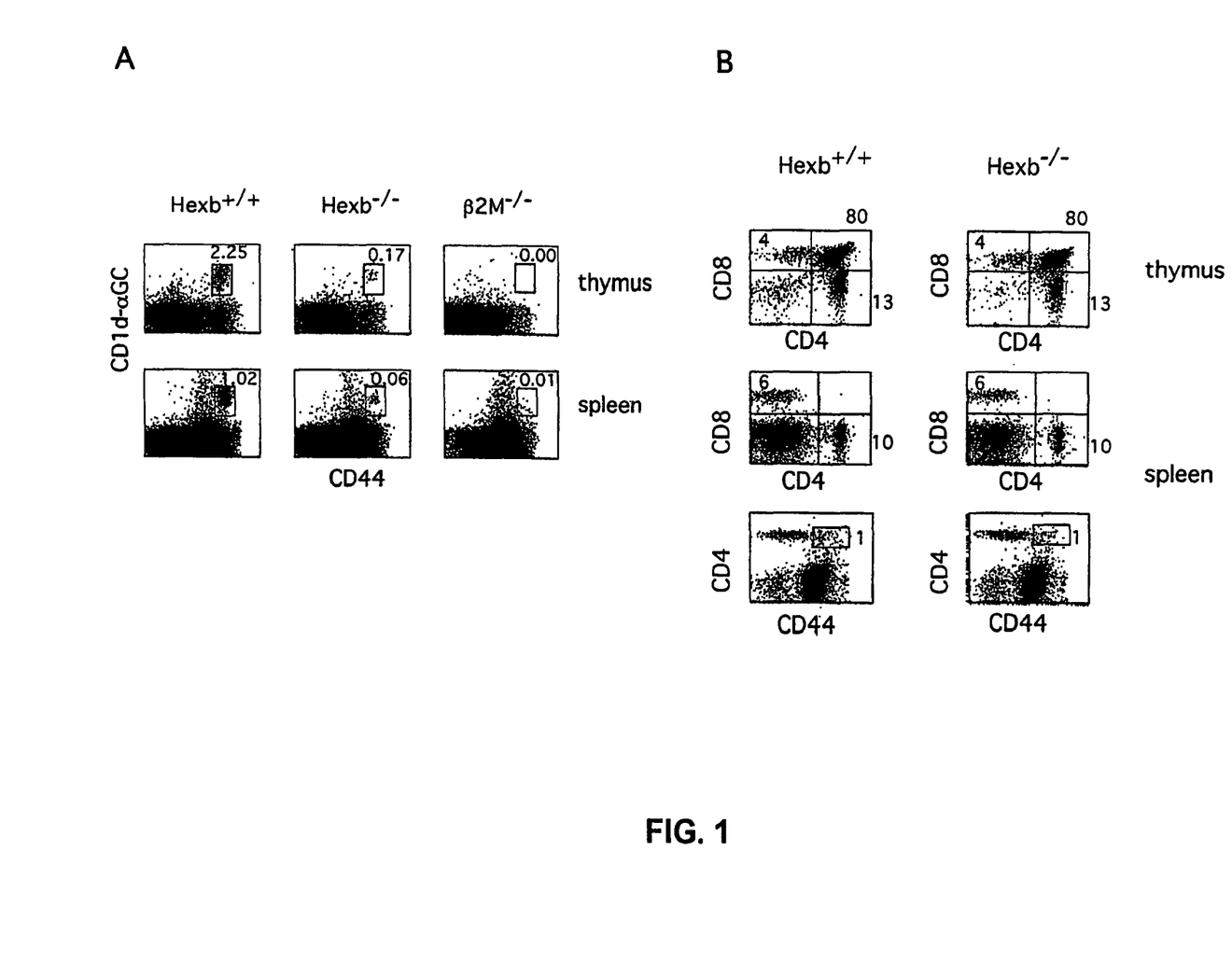
FIG. 1A presents representative FACS profiles demonstrating deficient thymic selection of V$\alpha$14 NKT cells in Hexb$^{-/-}$ mice. Percentages are indicated in the upper quadrants. The data are representative of 5 pairs of littermates examined in 3 separate experiments.
FIG. 1B presents representative FACS profiles of splenocytes and thymocytes stained for CD4/CD8 and CD4/CD44 in Hexb$^{-/-}$ mice.

Deficient Thymic Selection of Vα14 NKT Cells and Specific Antigen Presentation Defects in Hexb$^{-/-}$ Mice Lymphocytes from thymus and spleen of Hexb$^{-/-}$ and Hexb$^{-/-}$ littermates were stained with CD1d-αGalCer tetramers and anti-CD44. Absolute numbers of lymphocytes in the thymus and the spleen of mutant and wild type mice were similar. As shown in FIG. 1A, Hexb$^{-/-}$ mice, deficient in the lysosomal glycosphingolipid degrading enzyme β-Hexosaminidase b subunit, exhibited a severe reduction in Vα14 NKT cells. CD1d-αGalCer tetramer staining in both thymus and spleen was reduced to 5% of control littermates, close to the background level of mice deficient in CD1d expression such as β2-microglobulin$^{-/-}$ (β2M$^{-/-}$) mice or CD1d$^{-/-}$ mice (not shown). In contrast, as shown in FIG. 1B, the development of classical, naïve and memory CD4 and CD8 T cells, as well as B cells, γδ T cells and NK cells (not shown), was conserved.

Figure 2:
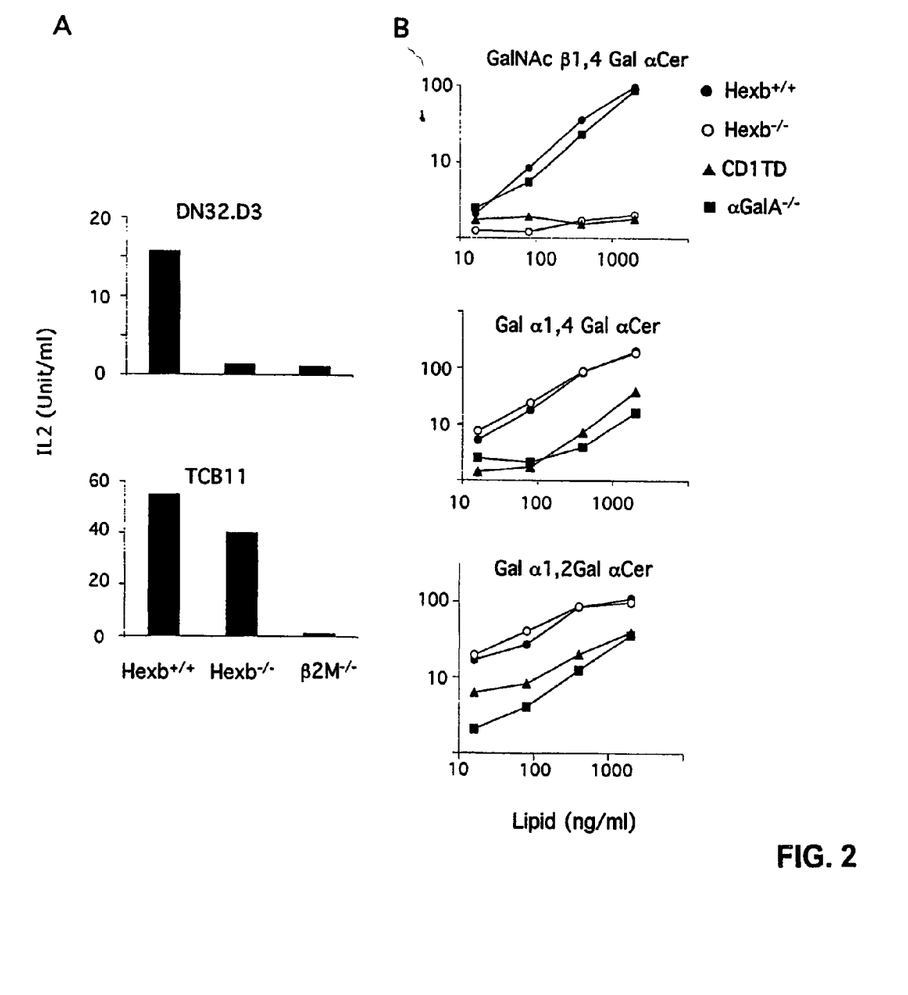
FIG. 2A depicts autoreactive responses of V$\alpha$14 DN32.D3 and non-V$\alpha$14 TCBII hybridomas against CD1d-expressing thymocytes from Hexb$^{-/-}$ and Hexb$^{-/-}$ littermates.
FIG. 2B depicts V$\alpha$14 DN32.D3 hybridoma stimulation responses to spleen cells from Hexb$^{-/-}$ (o) and Hexb$^{-/-}$ littermates (●), $\alpha$GalAl-(■) and CD1-TD knock-in (▲) mice. Spleen cells were pulsed with $\alpha$GalCer variants as indicated prior to hybridoma stimulation. The data are representative of 2 separate experiments.

While CD1d surface expression was unaltered, as shown in FIG. 2A, Hexb$^{-/-}$ cells failed to elicit a response from Vα14 NKT cell hybridoma DN32.D3. (β-2M$^{-/-}$ thymocytes lacking CD1d expression served as negative control). In contrast, the response of non-Vα14, CD1d autoreactive NKT hybridomas such as TCB 11 was conserved, suggesting a selective defect in the generation of the putative lysosomal ligands of Vα14 NKT cells.

Using a panel of diglycosylated derivatives of αGalCer requiring lysosomal processing into αGalCer prior to recognition by Vα14 NKT cells (as described in Prigozyet T I et al., Science 291, 664-7. (2001), incorporated herein by reference in its entirety) the lysosomal functions of Hexb$^{-/-}$ cells were further probed. As shown in FIG. 2B, consistent with the known substrate specificities of the corresponding enzymes, there was a selective defect in the presentation of GalNAc β1,4 Gal αCer by Hexb$^{-/-}$ cells, whereas, in contrast, α-Galactosidase A (αGalA)$^{-/-}$ cells showed a selective defect for Gal α1,4 Gal αCer and Gal α1,2 Gal αCer. These results demonstrate the specific nature of the antigen presentation defects associated with these mutations. As expected, CD1-TD 'knock-in' cells were markedly defective in the presentation of all of these complex glycolipids, due to impaired lysosomal recycling of CD1d bearing a truncation of the cytoplasmic endosomal targeting motif.

Example 3 iGb3 is the Ligand of mVα14 and hVα24 NKT Cells

Figure 3:
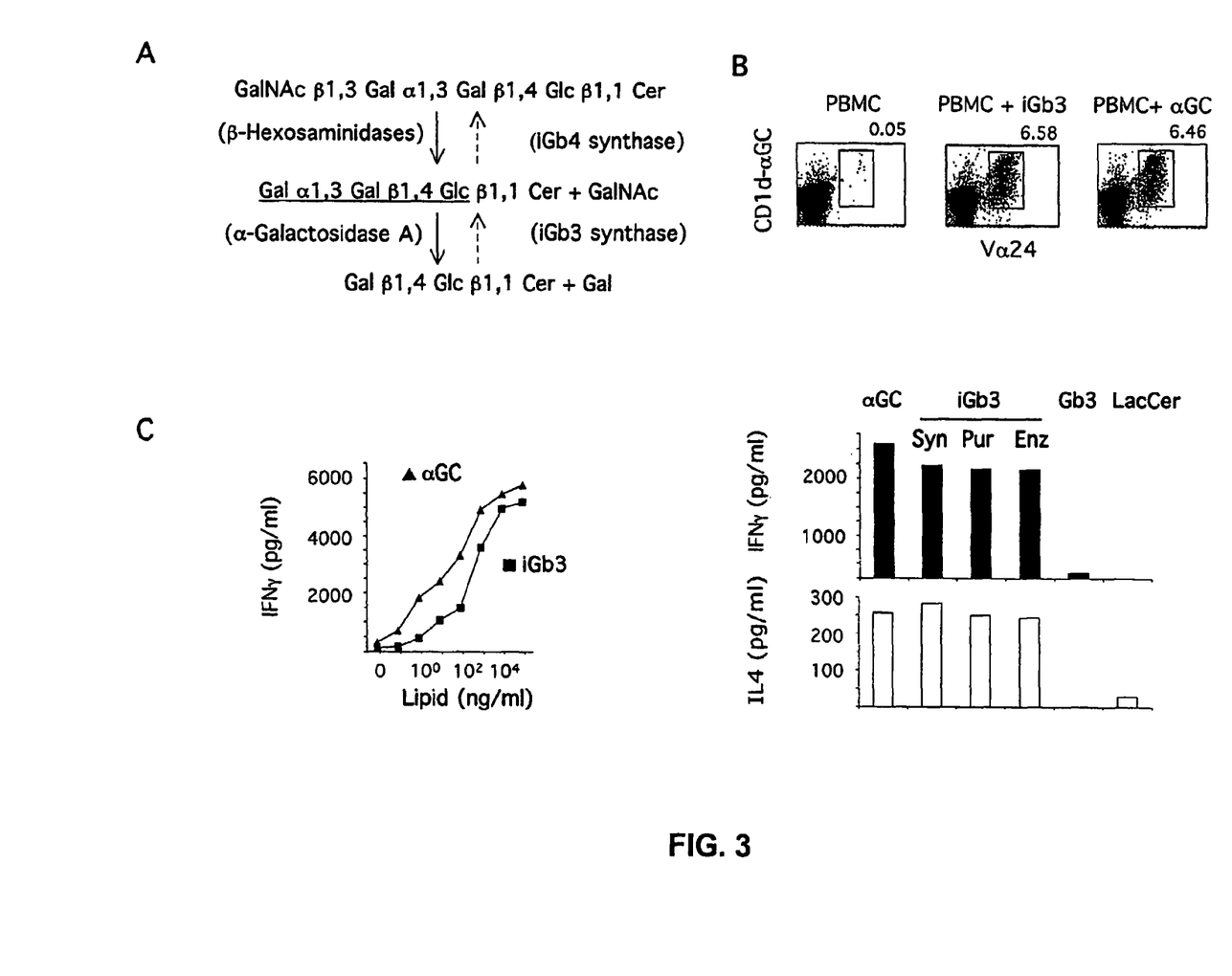
FIG. 3A is a schematic of synthesis of iGb3 in the Golgi (dotted arrows, right), and its degradation in the lysosome (continuous arrows, left). From top to bottom, iGb4, iGb3 and Lactosyl ceramide.
FIG. 3B depicts frequency of hV$\alpha$24 NKT PBL, doubly-stained by anti-V$\alpha$24 and CD1d-$\alpha$GalCer tetramers, in PBMC cultured for 4 days in the presence of 100 ng/ml $\alpha$GalCer, iGb3, or medium alone, as indicated.
FIG. 3C left panel depicts IFN-$\gamma$ production by a human V$\alpha$24 NKT line stimulated with a range of concentrations of iGb3 and $\alpha$GalCer in the presence of irradiated PBMC as CD1d-expressing antigen presenting cells. The right panel depicts IFN-$\gamma$ vs. IL-4 production by the human V$\alpha$24 NKT line in response to irradiated PBMC and 100 ng/ml of iGb3 of synthetic, purified and enzymatic origin, vs. 100 ng/ml of $\alpha$GalCer, Gb3 or LacCer, as indicated.
Figure 4:
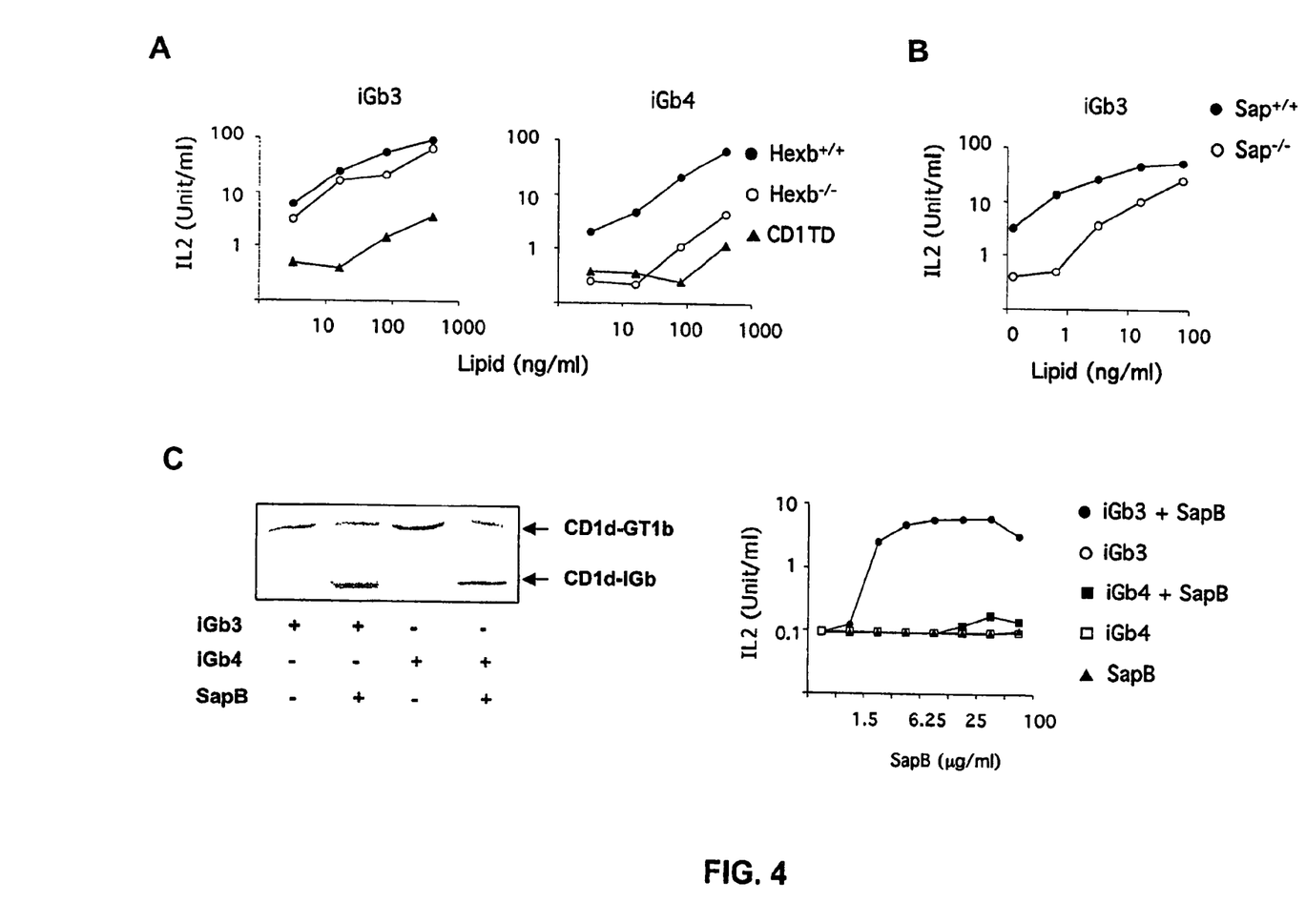
FIG. 4A depicts stimulation of mouse V$\alpha$14 hybridoma DN32.D3 by iGb3 and iGb4 with bone marrow-derived DC as CD1d-expressing antigen-presenting cells from Hexb$^{-/-}$, Hexb$^{-/-}$ and CD1-TD mice, as indicated.
FIG. 4B depicts stimulation of mouse V$\alpha$14 hybridoma DN32.D3 by iGb3 with bone marrow-derived dendritic cells from saposin deficient (Sap$^{-/-}$) and sufficient (Sap$^{-/-}$) littermates, as indicated.
FIG. 4C left panel depicts in vitro loading of iGb3 and iGb4 onto recombinant CD1d in the presence of saposin B, visualized by isoelectrofocusing. Electromobility shift indicates partial replacement of GTI b by iGb3 and iGb4, as indicated. The right panel shows cell-free presentation to DN32.D3 of iGb3 and iGb4 by plate-bound CD1d in the presence of saposin B, as indicated.

Chemically synthesized globotrihexosylceramide (Gb3, Gal α1,4 Gal β1,4 Glc β1,1 Cer) and isoglobotrihexosylceramide (iGb3, Gal α1,3 Gal β1,4 Glc β1,1 Cer) were tested for their ability to stimulate NKT cells in the presence of antigen-presenting cells. As shown in FIGS. 3-4, iGb3 alone was a potent stimulator of both human Vα24 and mouse Vα14 NKT cells. Like αGalCer, iGb3 selectively stimulated and expanded human Vα14 NKT cells in 4-day cultures of fresh PBMC (FIG. 3B). Synthetic iGb3 presented by irradiated PBMC stimulated potent Th1 (IFNγ) and Th2 (IL4) cytokine secretion by a polyclonal human NKT line (FIG. 3C, left and right panels) as well as 2/2 cloned CD4 and DN lines (not shown). iGb3 derived from other sources, including natural iGb3 purified from cat intestine, and iGb3 produced in vitro by action of iGb3 synthase on lactosylceramide and UDP-galactose, were stimulatory as well, eliciting Th1 and Th2 cytokines at levels comparable to αGalCer (FIG. 3C, right panel). iGb3 presented by CD1d-expressing bone marrow-derived dendritic cells stimulated the mVα14 NKT cell hybridoma DN32.D3 (FIG. 4A) as well as 5/5 other individual mVα14 hybridomas (not shown) and it failed to stimulate 3/3 non-Vα14 hybridomas (not shown).

Example 4 iGb4, but not LacCer, Stimulates NKT Cells

As shown in FIG. 4A, right panel, iGb4 presented by bone marrow-derived dendritic cells was stimulatory for mouse and human (not shown) whereas LacCer, which can also be generated by degradation of GM3, was not. Also shown in FIG. 4A, Hexb$^{-/-}$ cells presented iGb3 but failed to present iGb4 and CD1d trafficking to lysosomal compartment was essential to present these antigens due in part to the essential function of saposins (FIG. 4B). Thus, ligand recognition requires at least the three saccharide residues of the isoglobo-series.

In a cell-free assay, iGb3 and iGb4 both required saposin B to replace GT1b preloaded onto CD1d (FIG. 4C, left panel). Moreover, CD1d/iGb3 complexes directly stimulated Vα14 NKT cells (FIG. 4C, right panel). In contrast, CD1d/iGb4 only elicited a very weak response. Altogether, these results demonstrate that iGb3 is the direct ligand of the Vα14 NKT cell and that, in vivo, the distal saccharide residue of iGb4 had to be removed by action of β-Hexosaminidases in the lysosome prior to TCR recognition at the plasma membrane.

Example 5

Isolectin B4 Blocks NKT Cell Activation by iGb3

Figure 5:
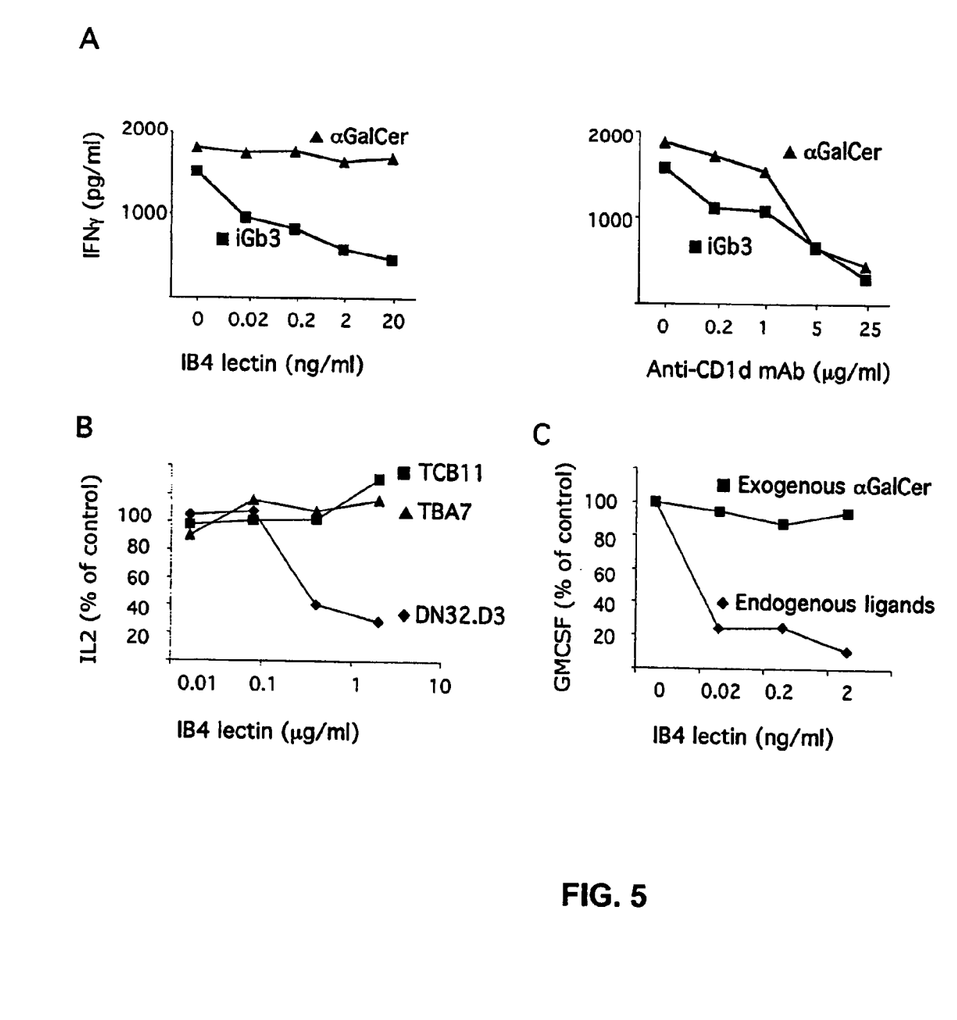
FIG. 5A left panel depicts specific inhibition by IB4 of the stimulation of the human V$\alpha$24 NKT line by iGb3 but not $\alpha$GalCer pulsed PBMC. The right panel shows inhibition by anti-human CD1 d mAb of both iGb3 and $\alpha$GalCer stimulation.
FIG. 5B depicts specific inhibition of the CD1d-autoreactive response of V$\alpha$14+DN32.D3 but not that of non-V$\alpha$14 hybridomas TCB 11 and TBA7 to RBL.CD1d by isolectin B4. Results are expressed as % control without lectin, and are representative of 4 separate experiments.
FIG. 5C depicts ELISA results (measured by as GMCSF release in the supernatant) demonstrating specific inhibition by IB4 of the CD1d-autoreactive response of the hV$\alpha$24 NKT line to PBMC-derived dendritic cells alone, but not the response to PBMC-derived dendritic cells plus exogenous αGalCer. Results are expressed as % control without lectin (i.e. 939 pg/ml for exogenous ligand and 294 pg/ml for endogenous ligand) and are representative of 3 separate experiments.

The block of Vα14 NKT cell development in Hexb$^{-/-}$ mice and the inability of Hexb$^{-/-}$ thymocytes to stimulate Vα14 NKT hybridomas suggested that iGb3 alone might be the main natural ligand of mVα14 and hVα24 NKT cells. This was tested using *Griffonia Simplicifolia* isolectin B4 (IB4), a lectin highly specific for terminal Gal α1,3 Gal as found in iGb3. As shown in FIG. 5A, IB4 impaired hVα24 NKT cell stimulation by exogenously added iGb3 but not αGalCer. In contrast, anti-CD1d mAb blocked stimulation by both glycolipids. These results were consistent with the specificity of IB4 and indicated that it recognized the terminal saccharides of iGb3 even when bound to CD1d, as might be expected from current structure models placing the saccharide residues outside of the groove of CD1 molecules exposed to recognition by TCR or lectin.

This property of IB4 was exploited to test whether terminal Gal α1,3 Gal residues contributed significantly to the natural stimulation of mVα14 and hVα24 NKT cells. As shown in FIG. 5B, IB4 impaired the natural autoreactive stimulation of DN32.D3 by RBL cells expressing mouse CD1d, whereas, as expected, the stimulation of control non-Vα14 CD1d autoreactive hybridomas such as TBA 7 and TCB 11 were unaffected. Furthermore, as shown in FIG. 5C, IB4 also blocked the natural recognition of CD1d-expressing PBMC-derived dendritic cells by the human Vα24 NKT line, but failed to block recognition of exogenously added αGalCer. Interestingly, IB4 blockade of iGb3 recognition in humans consistently required approx. 1000 times less lectin than in mouse (0.2 ng/ml vs 0.2 µg/ml, respectively). This is likely because mice, but not humans, express very abundant amounts of an additional IB4 ligand, the Gal α1,3 Gal epitope expressed on glycoproteins. Thus, the IB4 blocking experiments provided an independent confirmation of the prominent role of iGb3 as natural ligand of both mVα14 and hVα24 NKT cells.

Example 6

Synthesis of iGb3

Figure 7:
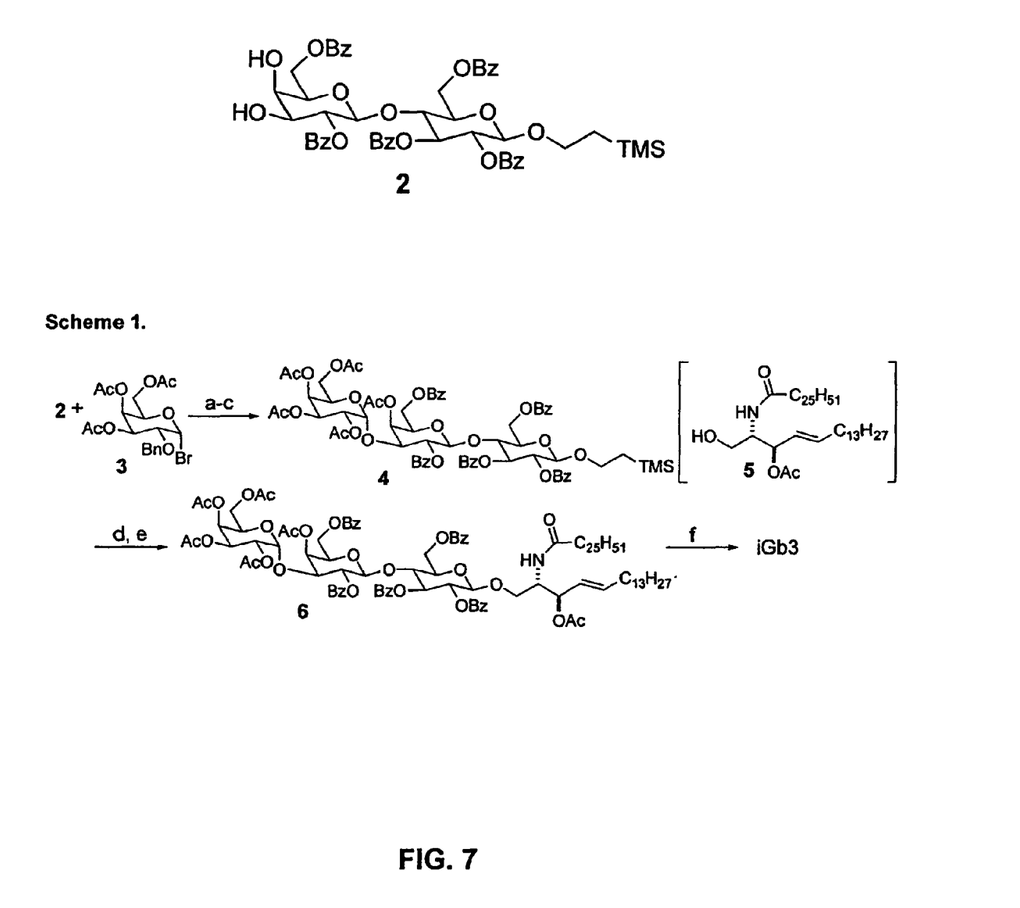
FIG. 7 depicts a suitable scheme for synthesis of iGb3.

Compound 2, shown in FIG. 7, was used as a starting material in the generation of iGb3. Synthetic scheme 1, also shown in FIG. 7, was initiated by coupling compound 2 with donor 3, followed by removal of the benzyl protecting group. The remaining alcohols were acylated to generate compound 4. The anomeric alcohol was liberated, and the trisaccharide was coupled to ceramide 5. Purification of compound 6, followed by deprotection gave iGb3 in good yield. Reagents used in Scheme 1 were as follows (yields in parentheses): a) AgOTf, 4 Å MS, $CH_2Cl_2$ (61%); b) H2, Pd/C (10%), EtOAc, EtOH (61%); c) $Ac_2O$, $Et_3N$, DMAP (95%); d) TFA, $CH_2Cl_2$ (99%); e1) $CCl_3CN$, $K_2CO_3$ e2) 5, $BF_3$-OEt, MS AW300, $CH_2Cl_2$; (45%); f) NaOMe, MeOH (86%).

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

The invention has been described with reference to various specific embodiments and techniques. However, it should be understood that many variations and modifications may be made while remaining within the spirit and scope of the invention.

We claim:

1. A method of activating an NKT cell comprising contacting the NKT cell in vitro with a sufficient amount of isoglobotrihexosylceramide (iGb3) to induce secretion of a cytokine from the NKT cell or upregulate expression of a cell surface marker on the NKT cell, wherein the iGb3 is presented to the NKT cell in complex with cell-free, recombinant CD1d that is multivalent.

2. The method of claim 1, wherein the iGb3 is purified.

3. The method of claim 1, wherein the iGb3 is synthetic.

4. The method of claim 1, wherein contacting the NKT cell comprises contacting a T cell receptor of the NKT cell.

5. The method of claim 1, wherein the NKT cell is cultured in vitro.

6. The method of claim 1, wherein the cytokine is selected from the group consisting of IL-1, IL-2, IL-4, IL-5, IL-6, IL-10, IL-13, TNF-α, TNF-β, IFN-γ and combinations thereof.

7. The method of claim 6, wherein the cytokine is IFN-γ.

8. The method of claim 6, wherein the cytokine is IL-2.

9. The method of claim 6, wherein the cytokine is IL-4.

10. The method of claim 1, wherein the cell surface marker is an IL-12 receptor or CD40L.

11. A method of inducing secretion of a cytokine from an NKT cell comprising contacting the NKT cell in vitro with iGb3, wherein the iGb3 is presented to the NKT cells in complex with cell-free, recombinant CD1d that is multivalent.

12. A method of upregulating expression of a cell surface marker on an NKT cell comprising contacting the NKT cell in vitro with iGb3, wherein the iGb3 is presented to the NKT cell in complex with cell-free, recombinant CD1d that is multivalent.

* * * * *